(12) United States Patent
Donovan

(10) Patent No.: US 6,641,820 B1
(45) Date of Patent: *Nov. 4, 2003

(54) CLOSTRIDIAL TOXIN DERIVATIVES AND METHODS TO TREAT PAIN

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/625,098

(22) Filed: Jul. 25, 2000

Related U.S. Application Data

(63) Continuation-in-part of application No. 09/489,667, filed on Jan. 19, 2000.

(51) Int. Cl.$^7$ .................. C07K 19/00; C07K 14/33; A61K 38/16

(52) U.S. Cl. .................. 424/239.1; 514/2; 514/12; 514/14; 530/350; 530/412; 435/69.1; 435/69.7; 435/70.1; 435/320.1; 435/325; 435/252.3

(58) Field of Search .................. 514/2, 12, 14; 530/350, 412; 435/69.7, 69.1, 320.1, 70.1, 325, 252.3; 424/239.1

(56) References Cited

U.S. PATENT DOCUMENTS

| 4,189,426 A | | 2/1980 | Li |
| 4,481,139 A | | 11/1984 | Folkers et al. |
| 4,664,911 A | | 5/1987 | Uhr et al. |
| 4,719,231 A | | 1/1988 | Umezawa et al. .......... 514/513 |
| 5,410,019 A | | 4/1995 | Coy et al. |
| 5,538,733 A | * | 7/1996 | Emory et al. .............. 424/450 |
| 5,714,468 A | | 2/1998 | Binder ..................... 514/14 |
| 5,744,131 A | | 4/1998 | Edwards et al. |
| 5,766,605 A | | 6/1998 | Sanders et al. |
| 5,846,216 A | | 12/1998 | Gonzales et al. .............. 604/2 |
| 5,853,695 A | * | 12/1998 | Srivastava et al. .......... 424/1.65 |
| 5,861,284 A | | 1/1999 | Nishimura et al. |
| 5,891,842 A | | 4/1999 | Kream |
| 5,965,406 A | | 10/1999 | Murphy |
| 5,989,545 A | | 11/1999 | Foster et al. |

FOREIGN PATENT DOCUMENTS

| WO | WO95/32738 | 12/1995 |
| WO | 9633273 | 10/1996 |
| WO | 9807864 | 2/1998 |
| WO | 9917806 | 4/1999 |

OTHER PUBLICATIONS

Morre et al., Treatment of Chronic Tennis Elbow with Botulinum Toxin. Lancet 349: 1746 (1997).*

XP001011356, Berge, O–G et al., "Selective Neurotoxic Lesions of Descending Serotonergic and Noradrenergic Pathways in the Rat"; Journal of Neurochemistry; 44(4):1156–1161 (1985).

XP001012206, Benoliel, R et al., "Actions of intrathecal diphtheria toxin–substance P fusion protein on models of persistent pain"; Pain; 79(2–3):243–253 (1999).

XP001011386, Garzon, J et al., "Effect of intrathecal injection of pertusis toxin on substance P norepinephrine and serotonin contents in various neural structures of arthritic rats"; Life Sciences; 47(21):1915–1924 (1990).

XP–000857076, Mosaic Structures of Neurotoxins Produced from Clostridium botulinum types C and D organisms, Moriishi et al., Biochimica et Biophysica Acta, 1307 (1996) 123–126.

XP–000869767, Intracellular Messengers Contributing to Persistent Nociception and Hyperalgesia Induced by L–Glutamate and Substance P in the Rat Formalin Pain Model, Terence J. Coderre, and Kiran Yashpal, European Journal of Neuroscience, vol. 6, pp. 1328–1334, 1994.

XP–002091075, Histochemical Localization of Galactose–Containing Glycoconjugates in Sensory Neurons and Their Processes in the Central and Peripheral Nervous System of the Rat, Wolfgang J. Streit, et al., The Journel of Histochemistry and Cytochemistry, vol. 33, No. 10, p.p 1042–1052, 1985.

Ueda, "In Vivo Molecular Signal Transduction . . . " Jpn J Pharmacol. vol. 79, 1999, pp 263–268.

Nichols et al, "Transmission of Chronic Nociception . . . " Science, vol. 286, Nov. 1999, pp. 1558–1561.

Lopes & Couture, "Localization of Bradykinin–Like . . . " Neuroscience, vol. 78, 1997, pp. 481–497.

Vigna et al, "Characterization of Antibodies . . . " J Nerosci, vol. 14, 1994, pp. 834–845.

Principles of Neural Science Third Edition, Edited by Kandel et al.

Babenko etal, "Experimental Human Muscle Pain . . . " Pain, vol. 82, 1999, pp. 1–8.

Garrison & Rall, "Autacoids; Drug Therapy of Inflammation".

Henry, "Substance P and Inflammatory . . . " Disease Therapy, 1993.

Tsuda et al "In Vivo Pathway . . . " Br J Pharmacol, vol. 127, 1999, pp 449–456.

Welch et al, "Sensitivity of Emryonic Rat . . . " Toxicon, vol. 38, 2000, pp 245–258.

(List continued on next page.)

Primary Examiner—Christopher S. F. Low
Assistant Examiner—Chih-Min Kam
(74) Attorney, Agent, or Firm—Stout, Uxa, Buyan & Mullins LLP; Frank J. Uxa

(57) ABSTRACT

Methods for treating a bone tumor, in particular pain associated with bone tumor, by administration to a patient of a therapeutically effective amount of an agent are disclosed. The agent may include a clostridial neurotoxin component attached to a targeting moiety, wherein the targeting moiety is selected from the group consisting of transmission compounds which can be released from neurons upon the transmission of pain signals by the neurons, and compounds substantially similar to the transmission compounds.

8 Claims, No Drawings

OTHER PUBLICATIONS

Mathias et al, "Topical Casaicin for Chronic Neck Pain.." Abstract,American Journal of Physical Medicine &Rehabilitation,vol. 74,1995,pp. 39–44.

Furst, "Transmitters Involved in Antinociception in the Spinal Cord" Abstract, Brain Research Bulletin, vol. 48, 1999, pp 129–141.

Poulain et al, Inhibition of Transmitter Release by Botulinum Neurotoxin A Eur.J.Biochem, vol. 185, 1989, pp. 197–203.

van Hagen et al, "Neuropeptides and Their Receptors" Ann Med, vol 31 Suppl2, pp. 15–22.

* cited by examiner

CLOSTRIDIAL TOXIN DERIVATIVES AND METHODS TO TREAT PAIN

CROSS REFERENCE

This application is a continuation-in-part of U.S. patent application Ser. No. 09/489,667, filed Jan. 19, 2000.

BACKGROUND

The present invention relates to methods for treating pain. In particular, the present invention relates to methods for treating pain associated with a bone tumor using a Clostridial toxin derivative.

Many, if not most ailments of the body cause pain. The causes of pain can include inflammation, muscle spasm, the onset of a neuropathic event or syndrome, and bone tumor.

Pain can be experienced when the free nerve endings which constitute the pain receptors in the skin as well as in certain internal tissues are subjected to mechanical, thermal or chemical stimuli. The pain receptors transmit signals along afferent neurons into the central nervous system and thence to the brain.

The transduction of sensory signals, such as pain signals, from the periphery to sensation itself is achieved by a multi-neuronal pathway and the information processing centers of the brain. The first nerve cells of the pathway involved in the transmission of sensory stimuli are called primary sensory afferents. The cell bodies for the primary sensory afferents from the head and some of the internal organs reside in various ganglia associated with the cranial nerves, particularly the trigeminal nuclei and the nucleus of the solitary tract. The cell bodies for the primary sensory afferents for the remainder of the body lie in the dorsal root ganglia of the spinal column. The primary sensory afferents and their processes have been classified histologically; the cell bodies fall into two classes: A-types are large (60–120 micrometer in diameter) while B-types are smaller (14–30 micrometer) and more numerous. Similarly the processes fall into two categories: C-fibers lack the myelin sheath that A-fibers possess. A-fibers can be further sub-divided into A beta-fibers, that are large diameters with well developed myelin, and A delta-fibers, that are thinner with less well developed myelin. It is generally believed that A beta-fibers arise from A-type cell bodies and that A delta—and C-fibers arise from B-type cell bodies.

After the activation of the primary sensory afferents the next step in the transduction of sensory signals is the activation of the projection neurons, which carry the signal, via the spinothalamic tract, to higher parts of the central nervous system such as the thalamic nuclei. The cell bodies of these neurons (other than those related to the cranial nerves) are located in the dorsal horn of the spinal cord. This is also where the synapses between the primary afferents and the projection neurons are located. The dorsal horn is organized into a series of laminae that are stacked, with lamina I being most dorsal followed by lamina II, etc. The different classes of primary afferents make synapses in different laminae. For cutaneous primary afferents, C-fibers make synapses in laminae I and II, A delta-fibers in laminae I, II, and V, and A beta-fibers in laminae III, IV, and V. Deeper laminae (V–VII, X) are thought to be involved in the sensory pathways arriving from deeper tissues such as muscles and the viscera.

The predominant neurotransmitters at the synapses between primary afferents and projection neurons are substance P, glutamate, calcitonin-gene related peptide (CGRP) and neuropeptide Y. The efficiency of transmission of these synapses can be altered via descending pathways and by local interneurons in the spinal cord. These modulatory neurons release a number of mediators that are either inhibitory (e.g. opioid peptides, glycine) or excitatory (e.g. nitric oxide, cholecystokinin), to provide a mechanism for enhancing or reducing awareness of sensations.

The bones of the mammalian skeleton are covered by a thick, fibrous membrane, the periosteum. Except for the richly innervated periosteum, bone is relatively insensitive to painful stimuli and surgical trauma can usually be inflicted upon bone with little or no patient discomfort. Even though bone is generally insensitive to pain, nerve fibers exist in bone, usually closely associated with blood vessels. Sherman, M. S. et al. *The Nerves of Bone*, J. Bone & Joint Surgery, 45-A(3);522–528:1963. The nerves in bone are apparently derived from the autonomic system and influence intraosseal blood flow as well as sensation of pressure and position. Halperin N., et al. Osteoid *Osteoma of the Proximal Femur Simulating Spinal Root Compression*, Clinical Orthopaedics & Related Research, 162;191–194;1982.

Thus, it is known that both bone and periosteum have both afferent sensory and efferent autonomic innervation. Hukkanen M., et al., *Rapid Proliferation of Calcitonin Gene-Related Peptide-Immunoreactive Nerves During Healing of Rat Tibial Fracture Suggests Neural Involvement in Bone Growth and Remodelling*, Neuroscience 54(4); 969–979:1993. See also O'Connell J. X. et al., *Osteoid Osteoma: The Uniquely Innervated Bone Tumor*, Mod Pathol 11(2);175–180:1998.

Bone tumors can arise from bone tissues as well as from nerves located within bone. Lichtenstein, L., *Classification of Primary Tumors of Bone*, Cancer 335–341;1951. Benign bone tumors of cartilaginous origin include enchondroma, osteochondroma, chondroblastoma and chondromyxoid. Benign bone tumors of bone tissue proper origin include osteoid osteoma and osteoblastoma.

Nerve fibers have been demonstrated within various bone tumors, including in the nidus of osteoid osteomas and in osteoblastomas. Schulman L. et al., *Nerve Fibers in Osteoid Osteoma*, J. Bone & Joint Surgery, 52-A(7); 1351–1356:1970. The nerve fibers within bone tumors are predominately non-myelinated, hence presumably arising from the sympathetic and/or parasympathetic nervous systems and are believed to have at least a vasomotor action upon tumor blood vessels. Additionally, myelinated nerve fibers located within bone tumors are postulated to function as afferent nociceptors. Greco F., et al., *Nerve Fibres in Osteoid Osteoma*, Int. J. Orthop Trauma, 16; 89–94:1988.

Typically, an intramedullary neoplasm will remain asymptomatic, even if rather large, until it breaks through the bone and contacts the periosteum. Osteoid osteomas are small, benign and richly vascularized bone neoplasms. Osteoid osteomas are rarely greater than one or two centimeters in diameter. Though surrounded by bone tissue and not in contact with the periosteum, even a small osteoid osteoma can cause intense throbbing pain. The pain generated by the presence of an osteoid osteoma can generally be relieved, at least to some extent, by oral salicyliates, such as aspirin. The pain can be described as local and more severe at night. Jaffe, H. L. Osteoid-Osteoma, Arch Surg 31;709–728:1935. Pain generated by a bone tumor if ineffectively treated, can limit function, reduce mobility, complicate sleep, and dramatically interfering with the quality of life.

It has been hypothesized that the pain which accompanies osteoid osteoma is due to vascular pressure changes within the neoplasm, presumably by direct stimulation of local nerves around intraosseous vessels. Sherman, M. S. et al., Mechanism of Pain in Osteoid Osteomas, Southern Medical Journal 58;163–166:1965.

Present methods for treating pain associated with bone tumors, whether by drugs or surgery, have many drawbacks and deficiencies. Thus, the typical oral, parenteral ortopical administration of an analgesic drug (such as a NSAID) to treat the symptoms of pain or of, for example, a salicylate, can result in widespread systemic distribution of the drug and undesirable side effects. Additionally, current drug therapy for bone tumor pain suffers from short drug efficacy durations which necessitate frequent drug re-administration with possible resulting drug resistance, antibody development and/or drug dependence and addiction, all of which are unsatisfactory. Furthermore, frequent drug administration increases the expense of the regimen to the patient and can require the patient to remember to adhere to a dosing schedule.

Surgical excision is unnecessary in the case of a benign bone tumor and should be avoided to prevent the bone destruction inevitable upon surgical removal and to avoid the risks attendant to surgical intervention. Additionally, surgery for a benign neoplasm can be refused by the patient or be contraindicated in a frail, elderly or osteoporeitic patient. Furthermore, the intramedullary nature of certain bone tumors can render them inoperable It has been reported (Nichols et al., *Science*, 1999; 286:1558–1561) (hereinafter "Nichols et al.") that intrathecal injection of a cytotoxic saporin-substance P (saporin can be abbreviated as "SAP" and substance P can be abbreviated as "SP") conjugate (which can be abbreviated as SAP-SP) results in a reduction of thermal hyperalgesia and mechanical allodynia.

Unfortunately, in employing SAP-SP to treat pain, the SAP-SP targeted neurons are killed by the SAP. For example, injection of SAP-SP may cause necrosis of other neurons through non-specific or low affinity SAP-SP neuronal interactions. For example, SAP-SP may interact with and cause motor neurons cell death. Since motor neurons and most other neurons in the spinal cord do not regenerate, it is contraindicated to use SAP-SP in humans, unless destruction of the neurons resulting in permanent disablement, and for example, paralysis, is a desired end result. Clearly it would be desirable to be able to treat pain, including pain associated with bone tumor, without causing necrosis and irreversible loss of the neurons treated.

Botulinum Toxin

The anaerobic, gram positive bacterium Clostridium botulinum produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (available from Allergan, Inc., of Irvine, Calif. as a purified neurotoxin complex under the trade name BOTOX®) is a $LD_{50}$ in mice (i.e. 1 unit). Thus, one unit of BOTOX® contains about 50 picograms of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg, which is about 12 times the primate $LD_{50}$ for botulinum toxin type A. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin/B/D,/F, and/G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype $C_1$ was originally thought to cleave syntaxin, but was found to cleave syntaxin and SNAP-25. Each toxin specifically cleaves a different bond (except tetanus and type B which cleave the same bond).

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (*Biochem J* 1;339 (pt 1): 159–65 (April 1999)), and synaptobrevin (*Mov Disord* 1995 May; 10(3): 376).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geqq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al., *Properties and use of Botulinum toxin and Other microbial Neurotoxins in Medicine*, Microbiol Rev. 56: 80–99 (1992). Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1\text{–}2 \times 10^8$ $LD_{50}$ U/mg or greater; purified botulinum toxin type B with an approximately 156 kD molecular weight with: a specific potency of $1\text{–}2 \times 10^8$ $LD_{50}$ U/mg or greater, and; purified botulinum toxin type F with an approximately 155 kD molecular weight with a specific potency of $1\text{–}2 \times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down , U.K.; Wako (Osaka, Japan), Metabiologics (Madison, Wis.) as well as from Sigma Chemicals of St Louis, Mo.

Pure botulinum toxin is so labile that it is generally not used to prepare a pharmaceutical composition. Furthermore, the botulinum toxin complexes, such a the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependent, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be stabilized with a stabilizing agent. The only successful stabilizing agent for this purpose has been the animal derived proteins albumin and gelatin. And as indicated, the presence of animal derived proteins in the final formulation presents potential problems in that certain stable viruses, prions or other infectious or pathogenic compounds carried through from donors can contaminate the toxin.

Furthermore, any one of the harsh pH, temperature and concentration range conditions required to lyophilize (freeze-dry) or vacuum dry a botulinum toxin containing pharmaceutical composition into a toxin shipping and storage format (ready for use or reconstitution by a physician) can detoxify some of the toxin. Thus, animal derived or donor pool proteins such as gelatin and serum albumin have been used with some success to stabilize botulinum toxin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of Clostridium botulinum grown in a medium containing N–Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX® sterile normal saline without a preservative; 0.9% Sodium Chloride Injection is used by drawing up the proper amount of diluent in the appropriate size syringe. Since BOTOX® is believed to be denatured by bubbling or similar violent agitation, the diluent is gently injected into the vial. BOTOX® should be administered within four hours after reconstitution. During this time period, reconstituted BOTOX® is stored in a refrigerator (20° to 8° C.). Reconstituted BOTOX® is clear, colorless and free of particulate matter. The vacuum-dried product is stored in a freezer at or below –5° C. BOTOX® is administered within four hours after the vial is removed from the freezer and reconstituted. During these four hours, reconstituted BOTOX® can be stored in a refrigerator (20° to 8° C.). Reconstituted BOTOX® is clear, colorless and free of particulate matter.

It has been reported that botulinum toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S 111–S115:1999), and in some circumstances for as long as 27 months. The Laryngoscope 109: 1344–1346:1999. However, the usual duration of a therapeutic effect of an intramuscular injection of Botox® is typically about 3 to 4 months.

Certain botulinum toxins have been used to treat various movement disorders, such as spasmodic muscle conditions with a resulting alleviation of pain. For example, it is known to use a botulinum toxin to treat muscle spasms with resulting relief from both the spasmodic muscle hyperactivity and from the pain which secondarily arises as a result of or due to the spasmodic muscle activity. For example, Cheshire et al., Pain, 59(1);65–69:1994 reported that patients with myofascial pain syndrome experienced a reduction of pain after injections of botulinum toxin type A to trigger points. See also WO 94/15629. It is believed that botulinum toxin A can reduce pain by reducing the sustained muscle contraction that caused or that substantially caused the pain in the first place. Thus, the pain which can result from or which can accompany a muscle spasm can be due to the lower, local pH caused by the spasm. An indirect effect of the flaccid muscle paralysis induced by a botulinum toxin is to permit the pH to return to a physiological level, thereby causing pain reduction as a secondary effect of the motor endplate cholinergic denervation which can result due to peripheral botulinum toxin administration.

Botulinum toxin can be used to treat migraine headache pain that is associated with muscle spasm, vascular disturbances, neuralgia and neuropathy. See e.g. U.S. Pat. No. 5,714,468. Notably, muscle spasm pain, hypertonic muscle pain, myofascial pain and migraine headache pain can all be due, at least in part, to the production and release of one or more nociceptive substances from the muscles themselves during periods of increased muscle tension or contraction.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX®(5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B. EurJ Neurol 1999 November; 6(Suppl 4):S3–S10.

In addition to having pharmacologic actions at the peripheral location, botulinum toxins may also have inhibitory effects in the central nervous system. Work by Weigand et al., Nauny-Schmiedeberg's Arch. Pharmacol. 1976; 292, 161–165, and Habermann, Nauny-Schmiedeberg'sArch. Pharmacol. 1974; 281, 47–56 showed that botulinum toxin is able to ascend to the spinal area by retrograde transport. As such, a botulinum toxin injected at a peripheral location, for example intramuscularly, may be retrograde transported to the spinal cord. However, the authors of the cited articles were unable to demonstrate that the radioalabelled material was intact botulinum toxin.

As discussed above, pain associated with muscle disorder, for example muscle spasm pain, and headache pain associated with vascular disturbances, neuralgia and neuropathy may be effectively treated by the use of botulinum toxin. However, there is a clear deficiency in available means for the treatment of an array of other types of pain. Such pain include, for example, pain associated with a bone tumor.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

U.S. Pat. No. 5,989,545 ("Foster et al.") (incorporated herein by reference in its entirety) discusses conjugating clostridial neurotoxins to targeting moieties in order to direct the inhibitory effect of clostridial neurotoxins toward primary sensory afferent neurons. Thus, the mechanism by which the agents disclosed by Foster et al. alleviate pain is as follows: the targeting moieties of the agents, for example the growth factors, bind to receptor sites on the sensory afferent nerve terminals, for example the growth factor receptors, in the spinal cord; then, the clostridial neurotoxins, along with the conjugated targeting moieties, translocate into the nerve terminal and inhibit the release of one or more transmitters involved in the signaling of pain, and thereby alleviate pain.

Unlike SAP-SP, the clostridial-targeting moiety conjugates disclosed by Foster et al. do not appear to be cytotoxic. However, despite their superiority to the SAP-SP in that they are non-cytotoxic, they are still inadequate as pain alleviating agents because they lack the specificity for treating pain. More particularly, the Foster et al.'s targeting moieties intended for primary sensory afferent neurons are non-specific.

Thus, the agents disclosed by Foster et al. are non-specific because their targeting moieties are not known to bind to receptors specifically and to primarily localize to primary sensory afferent nerve terminals. Therefore, the targeting moieties disclosed by Foster et al. may readily bind to receptors on neuronal terminals, or neurons, that are not primary sensory afferent synaptic terminals. For example, the targeting moiety comprising nerve growth factor disclosed by Foster et al. may readily bind to receptors on nerve terminals and neurons other than the receptors on the primary sensory afferent nerve terminals, because nerve growth factor receptors are found on most neurons. As such, the clostridial neurotoxin conjugate disclosed by Foster et al. may bind to one of these other neurons, for example the neurons involved in the sympathetic pathway, translocate into their cytosol, inhibit the release of their neurotransmitters, and thereby inhibiting their functions. Such random, non-specific inhibition may cause undesirable side effects during the treatment of pain.

Similarly, bradykinins, other targeting moieties disclosed by Foster et al., have been shown to have high density concentration in the motor neurons of the ventral horn in the spinal cord. (See Lopes et al., *Neuroscience* 78(2):481–497, the content of which is incorporated in its entirety herein by reference.) Agents disclosed by Foster et al. which bear bradykinins as targeting moieties may significantly interact and interfere with motor functions when the agents are injected intraspinally to treat pain.

Also, the opioid receptor binding targeting moieties disclosed by Foster et al., for example, methionine-enkephalin, are non-specific with respect to directing the clostridial neurotoxin to the primary sensory afferent nerve terminal. Kandel et al., *Prnciples of Neural Science*, third edition, page 395,(1991), indicated that opioid receptors are widely distributed through out the central nervous system, suggesting that opioid receptors, when activated, modulate physiological functions other than pain. Therefore, the clostridial neurotoxin-targeting moiety, as disclosed by Foster et al, may bind to and interfere with cells having opioid receptors but are not involved in the pain pathway. When this non-specific binding and interference occur, undesirous side effects may result.

What is needed therefore is an specific (high affinity) therapeutically effective, long duration non-cytotoxic agent and method for treating pain.

SUMMARY

Definitions

"Light chain" means the light chain of a clostridial neurotoxin. It has a molecular weight of about 50 kDa, and can be referred to as L chain, L or as the proteolytic domain (amino acid sequence) of a clostridial neurotoxin.

"Heavy chain" means the heavy chain of a clostridial neurotoxin. It has a molecular weight of about 100 kDa and can be referred to as H chain or as H.

"$H_C$" means a fragment (about 50 kDa) derived from the H chain of a clostridial neurotoxin which is approximately equivalent to the carboxyl end segment of the H chain, or the portion corresponding to that fragment in the intact H chain. It is believed to be immunogenic and to contain the portion of the natural or wild type clostridial neurotoxin involved in high affinity, presynaptic binding to motor neurons.

"$H_N$" means a fragment (about 50 kDa) derived from the H chain of a clostridial neurotoxin which is approximately equivalent to the amino end segment of the H chain, or the portion corresponding to that fragment in the intact in the H chain. It is believed to contain the portion of the natural or wild type clostridial neurotoxin involved in the translocation of the L chain across an intracellular endosomal membrane.

"LH$_N$" or "L-H$_N$" means a fragment derived from a clostridial neurotoxin that contains the L chain, or a functional fragment thereof coupled to the H$_N$ domain It can be obtained from the intact clostridial neurotoxin by proteolysis, so as to remove or to modify the H$_C$ domain.

"Targeting moiety" means a molecule that has a specific binding affinity for a cell surface receptor, for example, for a neuronal receptor so as to influence the transmission or reception of pain signals by the neuron.

"About" means approximately or nearly and in the context of a numerical value set forth herein means ±10% of the numerical value or range recited or claimed.

"Bone tumor" means a neoplasm located on or within a bone.

"Local administration" means direct administration by a non-systemic route at or in the vicinity of the site of an affliction, disorder or perceived pain.

Importantly, the agents disclosed herein are preferably administered by local administration, that is directly to the site where a therapeutic effect is desired.

The present invention meets this need by providing specific (high affinity) therapeutically effective, long duration non-cytotoxic agents and methods for treating pain. I have discovered agents effective for alleviating pain, particularly pain associated with bone tumor, and methods of using such agents to alleviate pain. The present invention provides non-cytotoxic agents for treating pain which preferably have one or more of the characteristics of long duration of activity and specificity for the treatment of pain with limited or substantially insignificant side effects at therapeutic dose levels. Furthermore, the methods of producing these agents are relatively straight forward and effective to provide the desired results.

In one broad aspect of the invention, agents are provided comprising a clostridial neurotoxin component coupled to a targeting moiety selected from the group consisting of transmission compounds released from neurons in transmitting pain signals and compounds substantially similar to the transmission compounds.

In one preferred embodiment, the clostridial neurotoxin component is covalently coupled to the targeting moiety. The clostridial neurotoxin component may, for example, be derived (i.e. made or secreted by) from *Clostridial beratti*, *Clostridial butyricum*, or *Clostridial botulinum*. More preferably, the clostridium neurotoxin component is derived from (that is, is made or secreted by) a *Clostridial botulinum* bacterium. Although it is preferable that botulinum neurotoxin type A is used, other types, for example, types B, C$_1$, D, E, F, G and mixtures thereof, may be employed.

The clostridium neurotoxin component preferably includes at least one of a heavy chain and a light chain of a clostridial neurotoxin. The clostridial neurotoxin component may comprise only fragments of the entire neurotoxin. For example, in one embodiment, the Hc of the neurotoxin is removed or modified. More preferably, the Hof the neurotoxin, such as botulinum toxin type A, is removed.

In another embodiment, the L chain of a clostridial neurotoxin, or a fragment of the L chain of a clostridial neurotoxin containing the endopeptidase activity, is covalently coupled to a targeting moiety. The covalent linkages used to couple the components of the agents may include appropriate spacer regions.

In a preferred embodiment, the agent comprises the H$_N$, the L chain and the targeting moiety, covalently linked together.

The targeting moiety preferably is derived from an amino acid. In one embodiment of the present invention, the targeting moiety is glutamate, since glutamate is recognized as a neurotransmitter that is released in the transmission of pain signals.

In another preferred embodiment, the amino acids from which the targeting moiety is derived link to form a peptide which is one of the peptides released for the transmission of pain signals. For example, such peptides include neuropeptide Y, calcitonin-gene related peptide (CGRP), substance P and the like, preferably substance P.

In another embodiment, the targeting moiety can be a transmission compound which is, or which is substantially similar to, a neurotransmitter, which is released by a neuron to initiate or to propagate the transmission of, or which facilitates the generation of, a pain signal. Thus, as used herein the phrase "transmission compound" means a compound which is made by a neuron and which is secreted or released extracellularly (e.g. into a synaptic cleft or synaptic gap) by the neuron. Additionally, the transmission compound is a nociceptive compound, meaning that the transmission compound has a significant influence upon the generation and/or perception of pain (i.e. a "pain signal") in response to a nociceptive event. A nociceptive event can be, for example, an inflammation, trauma, or a neuropathic syndrome. A preferred group of transmission compounds can be selected from the tachykinin family of which substance P is a member. Examples of such tachykinins include physalaemin, kassinin, uperolein, eledoisin, and substance K. Additionally, substance P precursors, fragments, analogues comprising at least one D-amino acid and analogues comprising a disulfide bond may also be used as a targeting moiety.

In one embodiment of the present invention, the agent comprises a clostridial neurotoxin component (i.e. L-H$_N$,) or parts thereof, covalently attached or coupled to substance P.

In a preferred embodiment of the present invention, the agent comprises a botulinum neurotoxin toxin type A, or parts thereof, covalently coupled to substance P. In an additional preferred embodiment of the present invention, the agent comprises botulinum toxin neurotoxin type A, wherein the H$_C$ of the botulinum neurotoxin type A is modified, more preferably removed or deleted, and the remaining toxin (i.e. with the H$_C$ removed) is then covalently coupled to substance P.

In another embodiment of this invention, the agent comprises an L chain of a clostridial neurotoxin, or a fragment of the L chain containing the endopeptidase activity, coupled to substance P. Preferably, the L chain or fragment of the L chain is derived from botulinum toxin type A.

The agents disclose herein comprise a polypeptide, with a first and second amino acid sequence regions. The first region preferably includes a first domain and a second domain. Preferably, the first domain comprises a targeting moiety, and the second domain comprises an H$_N$. The targeting moiety is the same as described above. The H$_N$ preferably is derived from *Clostridial botulinum* type A and is able to facilitate the transfer of the entire polypeptide, or portions of the polypeptide, preferably the second amino acid region, across an intracellular endosome membrane into the cytosol of the neuron.

The second amino acid sequence region preferably comprises the L chain. Without wishing to limit the invention to any particular theory or mechanism of operation, it is believed that the L chain is an effective therapeutic element having biological activity because, as discussed above, once it is translocated inside the neuron it interferes with the exocytosis process of a neurotransmitter.

In another broad aspect of this invention, the present agents are expressed recombinantly with the targeting moiety, as a fusion protein therefore.

In one embodiment, recombinant techniques are used to produce the clostridial neurotoxin components of the present agents. The technique includes generating genetic constructs which have codes for clostridial neurotoxins, modified clostridial neurotoxins, or fragments thereof. The genetic constructs are then fused with cloning vectors, such as plasmids, and are incorporated into a host cell for amplification. The expressed clostridial components can then be isolated by conventional and known techniques.

A clostridial neurotoxin expressed recombinantly without a targeting moiety can be chemically coupled to a targeting moiety (conjugate formation). Preferably, the linkages between the clostridial components and the targeting moieties include appropriate spacer regions.

In another embodiment, the genetic constructs include genes coding for both the clostridial neurotoxin components and the targeting moieties. Additionally, the genetic constructs may include genes coding for appropriate spacer regions between the clostridial neurotoxin components and the targeting moieties.

In another broad aspect of this invention, there are provided methods for treatment of a bone tumor. A preferable treatment of bone tumor includes the treatment of, for example, pain associated with the bone tumor, which comprise administering effective doses of the agents according to the invention. The routes of administration preferably include administration locally to the peripheral location of pain, particularly to a bone tumor or the vicinity of a bone tumor.

In one embodiment, the present agents in therapeutically effective amounts, for example, between about 1 U and about 10,000 U, can be administered, for example, to the bone tumor, to alleviate pain experienced by a mammal. Preferably the amounts are between about 10 U and about 3,000 U. More preferably the amount is between about 20 and 250 units, such about 50 U to 200 U or 70 U.

In a human patient, the therapeutically effective doses (for agents derived from botulinum toxin type A) are in the amounts between about $10^{-3}$ U/kg and about 200 U/kg. Preferably, the agents used are administered in amounts between about 1 U/kg and about 10 U/kg. More preferably, the agents are administered in amounts of about 3 U/kg. Significantly, the pain alleviating effect of the present agents can persist for between about 2–6 months per administration, preferably 2–30 months per administration.

Each and every feature described herein, and each and every combination of two or more of such features, is included within the scope of the present invention provided that the features included in such a combination are not mutually inconsistent.

Importantly, the agents disclosed herein are preferably administered by local administration, that is, directly to the site where a therapeutic effect is desired.

DESCRIPTION

This invention is based upon the discovery that a bone tumor, preferably pain associated with a bone tumor, may be treated by administration to a patient of an agent which comprises of a clostridial neurotoxin component and a targeting moiety, where the targeting moiety is selected from the group consisting of transmission compounds which can be released from a neuron upon the initiation, transmission of, or facilitation of the generation of, a pain signal by the neuron. Significantly, the agents of the present invention can alleviate pain without being cytotoxic to their target neurons. The mechanism of action for these agents in alleviating pain, particularly pain associated with bone tumor, is currently not fully understood.

The agents of this invention provide pain alleviating effects when locally applied to peripheral pain sites, for example to the bone tumor or the vicinity of the bone tumor. Without wishing to limit the invention to any particular theory or mechanism of operation, it is believed that these agents can bind, enter into and interfere with the function of primary sensory neurons at the peripheral sites to alleviate pain. Furthermore, it is believed that these agents may interfere with the functions of cells other than the primary sensory neurons which have receptors for transmission compounds released from neurons in transmitting pain signals, for example orphanin, substance P and/or kyotorphin. See Ueda, *Jpn J. Pharmacology*, 79(3): 263–268, the content of which is incorporated in its entirety herein by reference. For example, the agent may bind to the surface of mast cells, which have receptors for substance P, translocate and inhibit the release of histamine therefrom. The inhibition of histamine may reduce the transmission of pain signal because histamine is known to directly act on primary afferent neurons to elicit pain.

In addition to having pharmacologic actions at the peripheral location, the modified neurotoxin of the present invention may also have inhibitory effects in the central nervous system. Presumably the inhibitory effects on the central nervous system may result from the retrograde transport of the agent via the primary afferent. This hypothesis is supported by our experimental data which shows that BoNT/A is retrograde transported to the dorsal horn when the neurotoxin is injected peripherally. Moreover, work by Weigand et al., Nauny-Schmiedeberg's Arch. Pharmacol. 1976; 292, 161–165, and Habermann, Nauny-Schmiedeberg's Arch. Pharmacol. 1974; 281, 47–56, showed that botulinum toxin is able to ascend to the spinal area by retrograde transport. As such, an agent, for example botulinum toxin type A-substance P, injected at a peripheral location, for example at the bone tumor site, may be retrograde transported from the peripheral primary sensory terminal to the central primary sensory terminal.

Without wishing to limit the invention to any particular theory or mechanism of operation, it is believed that, at least with respect to areas in spinal cord, the agents disclosed herein target neurons having receptors for neurotransmitters that are released by neurons for or upon the transmission of pain signals. For example, when the targeting moiety is substance P, the agent is thought to interact with neurons expressing substance P receptors (SPR), such as projection neurons. Moreover, the receptors binding neurotransmitters released for the transmission of pain are primarily expressed on cells involved in the transmission of pain signals. For example, with respect to the central nervous system, it is well known that substance P receptors are primarily expressed on projection neurons in the dorsal horn of the spinal cord. See e.g. Vigna et al., *J Neuroscience*, 14(2): 834–845 (1994).

Therefore, the agents as described in this invention preferably are very specific for treating pain because they do not substantially or significantly interact and/or interfere with neurons and cells of other systems which may not be associated with the pain pathways and mechanisms. Moreover, it is believed that the agents of this invention may enter into these specific neurons, for example projection neurons, through an endocytosis process. Once inside the neurons, it is further believed that the $H_N$ of these agents facilitate the translocation of the agent into the cytosol. In the cytosol, the agent, or a component thereof, can inhibit the release of a neurotransmitter involved in the further transmission of pain signals. It is further believed that the L chain of the clostridial neurotoxin component of the agent is responsible for the inhibition of the release of neurotransmitters that are involved in pain transmission by interfering with their vesicular exocytosis.

According to one broad aspect of the invention, the clostridial neurotoxin component is covalently coupled to a targeting moiety. The clostridial neurotoxin component is a polypeptide and may be derived from *Clostridial beratti*, *Clostridial butyricum*, or *Clostridial botulinum*. More preferably, the clostridium neurotoxin component is derived from *Clostridial botulinum*. *Clostridial botulinum* produces botulinum toxin types A, B, $C_1$, D, E, F and G. Although any of these toxin types may be used in the present invention, botulinum type A is more preferably used.

Furthermore, the clostridial neurotoxin component may comprise only a fragment of the entire neurotoxin. For example, it is known in the art that the $H_C$ of the neurotoxin molecule can be removed from the other segment of the H chain, the $H_N$, such that the $H_N$ fragment remains disulphide linked to the L chain of the neurotoxin molecule to provide a fragment known as known as the $LH_N$. Thus, in one embodiment of the present invention the $LH_N$ fragment of a clostridial neurotoxin is covalently coupled, using linkages which may include one or more spacer regions, to a targeting moiety.

In another embodiment of the invention, the domain having the $H_C$ of a clostridial neurotoxin is removed, mutated or modified, e.g. by chemical modification, to reduce, or preferably incapacitate, its ability to bind the neurotoxin to receptors at the neuromuscular junction. This modified clostridial neurotoxin is then covalently coupled, using linkages which may include one or more spacer regions, to a targeting moiety.

In another embodiment of the invention, the H chain of a clostridial neurotoxin, in which the $H_C$ is removed, mutated or modified, e.g. by chemical modification, to reduce, preferably incapacitate, its ability to bind the neurotoxin to receptors at the neuromuscular junction is combined with the L-chain of a different clostridial neurotoxin, to form a hybrid. For example, in one embodiment, the clostridial neurotoxin component comprises an H chain with the $H_C$ removed, mutated or modified derived from botulinum toxin type A, and an L chain derived from another botulinum toxin type. The described hybrid is covalently coupled to a targeting moiety, preferably with one or more spacer regions.

In another embodiment of the invention the L chain of a clostridial neurotoxin, or a fragment of the L chain containing the endopeptidase activity, is linked, using linkages which may include one or more spacer regions, to a targeting moiety which can also effect the internalization of the L chain, or fragment thereof containing endopeptidase activity, into the cytoplasm of the cell.

In a preferred embodiment, the agent comprises the $H_N$, the L chain and the targeting moiety, covalently linked together. The targeting moiety according to the first aspect of the invention is preferably derived from amino acids, substituted counterparts thereof and mixtures thereof. The term "substituted counterparts thereof" as it relates to any of the above noted amino acids refers to molecules that are functionally and physically similar to the amino acids, either as independent units or units incorporated into macromolecules, for example, peptides.

In one preferred aspect of the present invention, the targeting moiety is glutamate, since glutamate is the predominant neurotransmitter at the synapses between primary afferents and projection neurons. In another embodiment, the targeting moieties may be components that are substantially similar to the transmission compounds, for example, glutamate, in this particular instance. Hereinafter, the term "components that are substantially similar to the transmission compounds," is defined as molecules or substances that have the same functions as that of the transmission compounds, for example, binding to receptors that are involved in the transmission of pain signals.

In one embodiment, components that are substantially similar to glutamate are agonists of glutamate. For example, components substantially similar to glutamate are quisqualate, DL-alpha-amino-3-hydroxy-5-methylisoxazole4-propionate, N-Me-D-aspartate, kinate and the like. Additionally, components substantially similar to glutamate may also include antagonists of glutamate. For example, these molecules include 6-cyano-7nitroquinozaline-2,3-dione, 3-(2-carboxypiperazin4-yl) propyl-1-phosponic acid, lactonized kainate and the like.

In a more preferred embodiment, the amino acids link to form one of the peptides which are released by neurons for the transmission of pain signals. For example, these peptides include neuropeptide Y and calcitonin-gene related peptide (CGRP). Even more preferably, the peptide is substance P.

In another embodiment, components substantially similar to substance P may be used as targeting moieties. These components include substance P precursors, fragments, analogs and/or derivatives. The history, isolation, identification, and synthesis of substance P and its precursors, fragments, analogs and/or derivatives are disclosed in U.S. Pat. No. 5,891,842 (incorporated herein by reference in its entirety)

Substance P is an 11 amino acid peptide which has a number of different natural and synthetic precursor forms; has been demonstrated to be converted into a variety of naturally occurring amino-terminal peptide fragments; and can be obtained in analog format compromising, substituted counterparts thereof, for example, lysine methyl ester, D-amino acids or disulfide bridges substitutions, thereby yielding more stable and discriminating formulations. A representative listing of substance P and its related chemical entities is provided by Table 1 below. The amino acid sequence (1) in Table 1 (Arg-Pro-Lys-Pro-Gln-Gln-Phe-Phe-Gly-Leu-Met-amide) can be referred to a SEQ ID NO: 1, and the subsequent 17 amino acid sequences set forth in Table one can be similarity identified as SEQ ID NO:2 to SEQ ID NO:18.

TABLE 1

Substance P, And Representative Precursors, Fragments, And Stabilized Or Substituted Analogs

| Name | Formula | |
|---|---|---|
| (1) Substance P | Arg-Pro-Lys-Pro-Gln-Gln-Phe-Phe-Gly-Leu-Met-amide | (SEQ ID NO: 1) |
| Natural Precursors | | |
| (2) Substance P-Glycine* | Arg-Pro-Lys-Pro-Gln-Gln-Phe-Phe-Gly-Leu-Met-Gly | (SEQ ID NO: 2) |
| (3) Substance P-Glycine-Lycine* | Arg-Pro-Lys-Pro-Gln-Gln-Phe-Phe-Gly-Leu-Met-Gly-Lys | (SEQ ID NO: 3) |
| (4) Substance P-Glycine-Lycine-Arginine* | Arg-Pro-Lys-Pro-Gln-Gln-Phe-Phe-Gly-Leu-Met-Gly-Lys-Arg | (SEQ ID NO: 4) |
| Carboxy-Ester Synthetic Precursors | | |
| (5) Substance P-Glycine Methyl Ester* | Arg-Pro-Lys-Pro-Gln-Gln-Phe-Phe-Gly-Leu-Met-Gly-OMe | (SEQ ID NO: 5) |
| (6) Substance P-Glycine-Lycine-Methyl Ester | Arg-Pro-Lys-Pro-Gln-Gln-Phe-Phe-Gly-Leu-Met-Gly-Lys-OMe | (SEQ ID NO: 6) |
| (7) Substance P-Glycine-Lycine-Arginine Methyl Ester* | Arg-Pro-Lys-Pro-Gln-Gln-Phe-Phe-Gly-Leu-Met-Gly-Lys-Arg-OMe | (SEQ ID NO: 7) |
| (8) Substance P-Glycine-Ethyl Ester* | Arg-Pro-Lys-Pro-Gln-Gln-Phe-Phe-Gly-Leu-Met-Gly-OEth | (SEQ ID NO: 8) |
| (9) Substance P-Glycine-Lysine Ethyl Ester* | Arg-Pro-Lys-Pro-Gln-Gln-Phe-Phe-Gly-Leu-Met-Gly-Lys-OEth | (SEQ ID NO: 9) |
| (10) Substance P-Glycine-Lysine-Arginine Ethyl Ester* | Arg-Pro-Lys-Pro-Gln-Gln-Phe-Phe-Gly-Leu-Met-Gly-Lys-Arg-OEth | (SEQ ID NO: 10) |
| Naturally-Occurring Amino-Terminal Peptide Fragments | | |
| (11) Substance P/1-4# | Arg-Pro-Lys-Pro | (SEQ ID NO: 11) |
| (12) Substance P/1-7# | Arg-Pro-Lys-Pro-Gln-Gln-Phe | (SEQ ID NO: 12) |
| (13) Substance P/1-9# | Arg-Pro-Lys-Pro-Gln-Gln-Phe-Phe-Gly | (SEQ ID NO: 13) |
| Analogs Comprising Synthetic D-Amino Acids Or Disulfide (Cys—Cys) Bridges | | |
| (14) [D-Pro2, D-Phe7, D-Trp9]-Substance P$^d$ | Arg-D-Pro-Lys-Pro-Gln-Gln-D-Phe-Phe-D-Trp-Leu-Met-amide | (SEQ ID NO: 14) |
| (15) [D-Pro2, D-Phe7, D-Trp9]-(Substance P-(Glycine$^d$ | Arg-D-Pro-Lys-Pro-Gln-Gln-D-Phe-Phe-D-Trp-Leu-Met-Gly | (SEQ ID NO: 15) |
| (16) [D-Pro2, D-Trp7, D-Trp9]-Substance P$^d$ | Arg-D-Pro-Lys-Pro-Gln-Gln-D-Trp-Phe-D-Trp-Leu-Met-amide | (SEQ ID NO: 16) |
| (17) [D-Pro2, D-Trp7, D-Trp9]-Substance P-Glycine$^d$ | Arg-D-Pro-Lys-Pro-Gln-Gln-D-Trp-Phe-D-Trp-Leu-Met-Gly | (SEQ ID NO: 17) |
| (18) [Cys3, Cys6, Tyr8, Pro10]-Substance P$^d$ | get,0001 | (SEQ ID NO: 18) |

*Shimonka et al., J. Neurochem. 59: 81–92 (1992).
$^a$Lee et al., Eur. J. Biochem. 114: 315–327 (1981); Pernow, B., Pharmacol. Rev. 35: 86–138 (1983); and Regoli et al., TIPS 9: 290–295 (1988).
Stewart et al., Nature 262: 784–785 (1986); and Skilling et al., J. Neurosci. 10: 1309–1318 (1990).
$^d$Lavielle et al., Biochem Pharmacol. 37:41 (1988); and Quirion, R. and T. V. Dam, Regulatory Peptides 22:18 (1988).

The components substantially similar to substance P may also include molecules in the same family as that of substance P. For example, a preferred family of such molecules would be the tachykinin family to which substance P is a member. Examples of some family members of tachykinins include physalaemin, kassinin, uperolein, eledoisin, substance K and the like.

In a preferred embodiment, the agent comprises a clostridial neurotoxin component, for example LH$_N$, coupled to substance P. In another preferred embodiment, the agent comprises a hybrid of two clostridial neurotoxins, such as the H chain, preferably H$_N$, derived from botulinum toxin A and the L chain derived from another botulinum toxin, coupled to substance P. In another preferred embodiment, the clostridial component of the agent is a botulinum toxin type A in which the H$_C$ has been removed or modified, coupled to substance P.

In another preferred embodiment, the agent comprises an L chain of a clostridial neurotoxin, or a fragment of the L chain containing the endopeptidase activity, coupled substance P. Even more preferably, the L chain or fragment of the L chain is derived from botulinum toxin A, and is coupled to substance P. Additionally, it is preferred that the L chain coupled to the substance P is covalently linked to H$_N$.

The clostridial components and the targeting moieties are coupled by covalent linkages. In a preferred embodiment, the linkages may include appropriate spacer regions. Spacer regions have many functions within this invention. For example, one of the functions of the spacer regions is to provide for adequate distance between the clostridial neurotoxin components and the targeting moieties so that the two components can independently and freely move about, without an internal steric hindrance.

In one embodiment, the spacer region is made up of sugar molecules, for example, saccharides, glucose, etc. In another embodiment, the spacer region may be constructed from an aliphatic chain. In another embodiment, the spacer regions may be constructed by linking together a series of amino acids, preferably glycine because they are small and are devoid of any functional group. In yet another embodiment, the spacer region may comprise one or more of the sugar molecules, aliphatic chains, and amino acids.

Also, these agents can be thought of as being polypeptides, with a first and a second amino acid sequence region. The first region preferably includes a first domain and a second domain. Preferably, the first domain of the first amino acid sequence comprises a targeting moiety. In one embodiment, the targeting moiety is able to bind to surface receptors of the spinal cord neurons under physiological conditions. More preferably, the targeting moiety specifically binds a receptor on a spinal cord dorsal horn neuron, for example a projection neuron.

Preferably, the second domain comprises a heavy chain or a portion thereof of a clostridial neurotoxin. Even more preferably, the H$_N$ of the heavy chain is able to facilitate the transfer of the polypeptide across an endosome membrane into the cytosol of the neuron. In one embodiment, the second domain of the first amino acid sequence comprises a clostridial neurotoxin heavy chain. More preferably, the clostridial neurotoxin heavy chain is derived from *Clostridium botulinum* neurotoxin type A. Even more preferably, the heavy chain is derived from the H$_N$ of *Clostridium botulinum* neurotoxin type A. In yet another embodiment, the heavy chain may be derived from *Clostridial botulinum* types B, $C_1$, D, E, F, G and mixtures thereof. Also, the heavy chain may be derived from *Clostridial baratii* and *Clostridial butyricum*. Additionally, the heavy chain, preferably the $H_N$, may be derived from *Clostridial tetani*.

The second amino acid sequence region preferably comprises the L chain. The L chain is the effective therapeutic element having biological activity because, as discussed above, once it is transferred inside the neuron it interferes with the exocytosis process of neurotransmitter. Preferably, the light chain is derived from *Clostridial botulinum* neurotoxin type A. According to another broad aspect of this invention recombinant techniques are used to produce the clostridial neurotoxin components of the agents. The technique includes steps of obtaining genetic materials from either DNA cloned from natural sources, or synthetic oligonucleotide sequences, which have codes for clostridial neurotoxin components including clostridial neurotoxins, modified clostridial neurotoxins and fragments thereof. The genetic constructs are incorporated into host cells for amplification by first fusing the genetic constructs with a cloning vectors, such as phages or plasmids. Then the cloning vectors are inserted into hosts, preferably *E. coli's*. Following the expressions of the recombinant genes in host cells, the resultant proteins can be isolated using conventional techniques. The clostridial neurotoxin components derived from the recombinant techniques can then be chemically coupled to targeting moieties. Preferably, the linkages between the clostridial components and the targeting moieties include an appropriate spacer regions.

In another embodiment, the genetic constructs include genes coding for both the clostridial neurotoxin components and the targeting moieties, for example, forming fusion proteins. Additionally, the genetic constructs may include genes coding for appropriate spacer regions between the clostridial neurotoxin components and the targeting moieties. From this aspect, the agents may be thought of as polypeptides comprising a first amino acid sequence region and a second amino acid sequence region. The first region may further comprise a first domain and a second domain. The details of these regions and domains are described above.

In another embodiment, the required $L-H_N$, which may be a hybrid of an L chain and an $H_N$ from different clostridial toxin types, is expressed recombinantly as a fusion protein. Such $LH_N$ hybrid may also be coupled to the targeting moiety, which may further include one or more spacer regions between them.

In another embodiment of the invention the L chain of a clostridial neurotoxin, or a fragment of the L chain containing the endopeptidase activity, is expressed recombinantly as a fusion protein with the $H_N$ of the H chain and the targeting moiety which can also affect the internalization of the L chain, or fragment thereof containing the endopeptidase activity, into the cytoplasm of the cell. The expressed fusion protein may also include one or more spacer regions.

There are many advantages to producing these agents recombinantly. For example, production of neurotoxin from anaerobic Clostridium cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous clostridial proteases through a process termed nicking. This involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the type and amounts of proteolytic activity produced by a given strain. For example, greater than 99% of *Clostridial botulinum* type A single-chain neurotoxin is activated by the Hall A *Clostridial botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered clostridial toxins is, therefore, an important consideration for manufacture of these materials. It would be a major advantage if neurotoxins such as botulinum toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in E.coli and purification of individual H and L chains of tetanus and botulinum toxins; these isolated chains are, by themselves, non-toxic; see Li et al., *Biochemistry* 33:7014–7020 (1994); Zhou et al., Biochemistry 34:15175–15181 (1995), hereby incorporated by reference herein. Following the separate production of these peptide chains and under strictly controlled conditions the H and L subunits can be combined by oxidative disulphide linkage to form the neuroparalytic di-chains.

In another broad aspect of this invention, methods are provided for the treatment of a bone tumor which comprise administering effective doses of the agents according to the invention. In a preferred embodiment, methods are provided for the treatment of pain associated with a bone tumor. The agents described in this invention can be used in vivo, either directly formulated or as a pharmaceutically acceptable salt, for treatment of pain.

Preferably, clostridial neurotoxin components of agents used to practice a method within the scope of the present invention comprise botulinum toxins, such as one of the type A, B, $C_1$, D, E, F or G. Preferably, the botulinum toxin used is botulinum toxin type A, because of its high potency in humans and ready availability. The targeting moiety of the agents used to practice the method herein is preferably a substance P.

In one aspect of the invention, there are provided methods for treatment of pain which comprise locally administering directly to a painful, benign bone tumor of a human patient therapeutically effective doses of an agent in accordance with this invention.

Preferably, the agent is used at a concentration of between about 10 and about 500 units per bone tumor injected. More preferably, the agent is used at a concentration of between about 100 and about 20,000 units per bone tumor injected. Alternatively, the agent may be administered in the amount between about 0.01 U/kg and about 200 U/kg.

Examples of neoplasms which can be treated according to the present invention are benign bone tumors of cartilaginous origin such as enchondroma, osteochondroma, chondroblastoma and chondromyxoid, all of cartilaginous origin, as well as benign bone tumors of bone origin include osteoid osteoma and osteoblastoma. An agent, such as a botulinum toxin-substance P can require, according to the methods of the present invention, from about 1 to 7 days to achieve an antinociceptive or to begin to achieve a necrotic effect upon a bone tumor. Thus, malignant bone tumors are excluded from the scope of the present invention because such tumors are preferably treated by a protocol with immediate effect such as surgical excision or radiotherapy, so as to prevent the tumor metastasizing.

Additionally, an agent according to the present invention is always locally administered in vivo directly to the site of the tumor, whether on or within a bone. Known local drug administration methods suitable for this purpose include by long needle for bolus injection and by insertion of a controlled release implant. Systemic routes of drug administration such as oral or intravenous administration are excluded from the scope of the present invention because systemic distribution of a neurotoxin is not desirable.

The present invention includes within its scope the use of any agent which has a long duration antinociceptive effect when applied peripherally or locally into a patient. For example, agents having the clostridial neurotoxin components made by any of the species of the toxin producing Clostridium bacteria, such as *Clostridium botulinum, Clostridium butydcum, Clostridium beratti* and *Clostridium tetani* can be used or adapted for use in the methods of the present invention. Additionally, all of the botulinum serotypes A, B, $C_1$, D, E, F and G can be advantageously used in the practice of the present invention, although type A is the most preferred and type B the least preferred, as explained above. Practice of the present invention can provide an analgesic effect, per injection, for 2 months or longer, for example 6 to 30 months, in humans.

EXAMPLES

The following examples provide those of ordinary skill in the art with specific preferred methods within the scope of the present invention to treat pain associated with a bone tumor and are not intended to limit the scope of the invention.

Example 1

Treatment of Osteoid Osteoma With Botulinum Toxin Type A

A 24 year-old female presents with a four month history of pain in the right buttock radiating to the lateral aspect of her thigh and leg. The pain is throbbing in nature and awakens her at night. It is aggravated by exercise and partially alleviated by aspirin. Examination reveals a full range of hip motion. Routine lab values (hematocrit, WBC, etc.) and CSF content are normal. Pelvic X-rays reveal a small, oval lesion at the base of the right femoral neck. A diagnosis of osteoid osteoma is made. Under radiographic guidance 50 units of an agent comprising an $LH_N$ (derived from botulinum toxin type A)—substance P is injected directly into the tumor. Within 1 to 7 days the pain has been substantially alleviated and the patient remains asymptomatic thereafter. Radiography and bone aspiration biopsy at 3 months post injection fails to reveal any evidence of the neoplasm.

Example 2

Treatment of Osteoid Osteoma With Botulinum Toxin Type B

A 13 year-old boy is admitted with a three month history of gnawing, persistent pain in his left thigh. The pain is more pronounced at night. Both the boy and his parents deny trauma. Physical examination reveals a healthy boy in no acute distress. Both hip joints have a full range of motion. The left thigh is tender. The left patellar reflex is absent and the ankle jerk somewhat diminished. Plantar responses are both flexor. Routine lab values, electromyography, spinal fluid content and pantopaque myelography are all normal. X-rays reveal a small, oval, lytic lesion situated below the lesser trochanter. A diagnosis of osteoid osteoma is made. 2500 units an agent comprising an $LH_N$ (derived from botulinum toxin type B)—substance P preparation is injected directly into the tumor. Within I to 7 days the pain has been substantially alleviated and the patient remains asymptomatic. Radiography and bone aspiration biopsy at 3 months post injection fails to reveal any evidence of the neoplasm.

Example 3

Treatment of Osteoid Osteoma With Botulinum Toxin Type $C_1$

A 58 year-old female is diagnosed with osteoid osteoma. Between about $10^{-3}$ U/kg and about 35 U/kg of an agent, for example, between about 10 units and about 10,000 units of an agent comprising an $LH_N$ (derived from botulinum toxin type $C_1$)—substance P is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 4

Treatment of Osteoid Osteoma With Botulinum Toxin Type D

A 56 year-old obese female is diagnosed with osteoid osteoma. Between about $10^{-3}$ U/kg and about 35 U/kg of an agent, for example, between about 10 units and about 10,000 units of an agent comprising an $LH_N$ (derived from botulinum toxin type D)—substance P is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 5

Treatment of Osteoid Osteoma With Botulinum Toxin Type E

A 61 year-old female is diagnosed with osteoid osteoma. Between about $10^{-3}$ U/kg and about 35 U/kg of an agent, for example, between about 10 units and about 10,000 units of an agent comprising an $LH_N$ (derived from botulinum toxin type E)—substance P is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 6

Treatment of Osteoid Osteoma With Botulinum Toxin Type F

A 52 year-old male is diagnosed with osteoid osteoma. Between about $10^{-3}$ U/kg and about 35 U/kg of an agent, for example, between about 10 units and about 10,000 units of an agent comprising an $LH_N$ (derived from botulinum toxin type F)—substance P is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 7
Treatment of Osteoid Osteoma With Botulinum Toxin Type G

A 14 year-old male is diagnosed with osteoid osteoma. Between about $10^{-3}$ U/kg and about 35 U/kg of an agent, for example, between about 10 units and about 10,000 units of an agent comprising an $LH_N$ (derived from botulinum toxin type G)—substance P is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 8
Treatment of Osteoblastoma With Botulinum Toxin Type A-G

A 19 year old male presents with a two month history of persistent pain in the right shoulder Examination reveals a full range of shoulder motion. Routine lab values (hematocrit, WBC, etc) and CSF content are normal. X-rays reveal a small, oval lesion at the base of the scapula and exploratory biopsy confirms a diagnosis of osteoblastoma. Under radiographic guidance between about $10^{-3}$ U/kg and about 200 U/kg of an agent comprising an $LH_N$ (derived from botulinum toxin type A, B, $C_1$, D, E, F or G)—substance P, for example, an agent comprising a $LH_N$ (derived from botulinum toxin type A)-substance P, is injected directly into the tumor. Within 1 to 7 days the pain has been substantially alleviated and the patient remains asymptomatic. Radiography and bone aspiration biopsy at 3 months post injection fails to reveal any evidence of the neoplasm.

Methods according to the invention disclosed herein has many advantages, including the following:

(1) the invention renders unnecessary many surgical procedures for effective treatment of a benign bone tumor.

(2) systemic drug effects can be avoided by direct local application of an agent according to the present invention.

(3) the ameliorative effects of the present invention can persist from about 2 months to about 6 months, or longer, for example, 30 months from a single local administration of an agent as set forth herein, and can be permanent upon necropsy of the tumor.

Although the present invention has been described in detail with regard to certain preferred methods, other embodiments, versions, and modifications within the scope of the present invention are possible. For example, a wide variety of neurotoxins can be effectively used in the methods of the present invention in place of clostridial neurotoxins. Additionally, the present invention includes local administration methods wherein two or more agents, such as two or more agents comprising different clostridial toxin components and targeting moieties, are administered concurrently or consecutively. For example, an agent comprising a $LH_N$ (botulinum neurotoxin type A)-substance P can be administered locally until a loss of clinical response or neutralizing antibodies develop, followed by administration of an agent comprising L-$H_N$ (derived from a botulinum neurotoxin type E)—substance P. While this invention has been described with respect to various specific examples and embodiments, it is to be understood that the invention is not limited thereto and that it can be variously practiced with the scope of the following claims.

SEQUENCE LISTING

```
<160> NUMBER OF SEQ ID NOS: 18

<210> SEQ ID NO 1
<211> LENGTH: 11
<212> TYPE: PRT
<213> ORGANISM: Unknown Organism
<220> FEATURE:
<223> OTHER INFORMATION: Description of Unknown Organism: This fragment
      is a substance P and is very well known in the art.
<220> FEATURE:
<221> NAME/KEY: MOD_RES
<222> LOCATION: (11)
<223> OTHER INFORMATION: Xaa at position 11 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16

<400> SEQUENCE: 1

Arg Pro Lys Pro Gln Gln Phe Phe Gly Leu Xaa
 1               5                  10

<210> SEQ ID NO 2
<211> LENGTH: 12
<212> TYPE: PRT
<213> ORGANISM: Unknown Organism
<220> FEATURE:
<223> OTHER INFORMATION: Description of Unknown Organism: Precursor to
      substance P, which is very well known in the art.
```

```
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Shimonka, et al.
<303> JOURNAL: J. Neurochem.
<304> VOLUME: 52
<306> PAGES: 81-92
<307> DATE: 1992

<400> SEQUENCE: 2

Arg Pro Lys Pro Gln Gln Phe Phe Gly Leu Met Gly
  1               5                  10

<210> SEQ ID NO 3
<211> LENGTH: 13
<212> TYPE: PRT
<213> ORGANISM: Unknown Organism
<220> FEATURE:
<223> OTHER INFORMATION: Description of Unknown Organism: This fragment
      is a precursor to substance P and is very well known in the art.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Shimonka, et al.
<303> JOURNAL: J. Neurochem.
<304> VOLUME: 52
<306> PAGES: 81-92
<307> DATE: 1992

<400> SEQUENCE: 3

Arg Pro Lys Pro Gln Gln Phe Phe Gly Leu Met Gly Lys
  1               5                  10

<210> SEQ ID NO 4
<211> LENGTH: 14
<212> TYPE: PRT
<213> ORGANISM: Unknown Organism
<220> FEATURE:
<223> OTHER INFORMATION: Description of Unknown Organism: This fragment
      is a precursor to substance P and is very well known in the art.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Shimonka, et al.
<303> JOURNAL: J. Neurochem.
<304> VOLUME: 52
<306> PAGES: 81-92
<307> DATE: 1992

<400> SEQUENCE: 4

Arg Pro Lys Pro Gln Gln Phe Phe Gly Leu Met Gly Lys Arg
  1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: This
      fragment is a carboxy-ester synthetic precursor to substance P.
<220> FEATURE:
<221> NAME/KEY: MOD_RES
<222> LOCATION: (12)
<223> OTHER INFORMATION: Xaa at position 12 is Glycine Methyl Ester;
<300> PUBLICATION INFORMATION:
<310> PATENT DOCUMENT NUMBER: 5891842
<311> PATENT FILING DATE: 1996-04-12
```

```
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 5

Arg Pro Lys Pro Gln Gln Phe Phe Gly Leu Met Xaa
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: This is a
      carboxy-ester synyhetic precursor to substance P.
<220> FEATURE:
<221> NAME/KEY: MOD_RES
<222> LOCATION: (13)
<223> OTHER INFORMATION: Xaa at position 13 is Lysine Methyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 6

Arg Pro Lys Pro Gln Gln Phe Phe Gly Leu Met Gly Xaa
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (14)
<223> OTHER INFORMATION: Xaa at position 14  is Arginine Methyl Ester;
<300> PUBLICATION INFORMATION:
<310> PATENT DOCUMENT NUMBER: 5891842
```

```
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 7

Arg Pro Lys Pro Gln Gln Phe Phe Gly Leu Met Gly Lys Xaa
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (12)
<223> OTHER INFORMATION: Xaa at position 12 is Glycine Ethyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 8

Arg Pro Lys Pro Gln Gln Phe Phe Gly Leu Met Xaa
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (13)
<223> OTHER INFORMATION: Xaa at position 13 is Lysine Ethyl Ester;
<300> PUBLICATION INFORMATION:
```

```
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 9

Arg Pro Lys Pro Gln Gln Phe Phe Gly Leu Met Gly Xaa
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (14)
<223> OTHER INFORMATION: Xaa at position 14  is Arginine Ethyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 10

Arg Pro Lys Pro Gln Gln Phe Phe Gly Leu Met Gly Lys Xaa
 1               5                  10

<210> SEQ ID NO 11
<211> LENGTH: 4
<212> TYPE: PRT
<213> ORGANISM: Unknown Organism
<220> FEATURE:
<223> OTHER INFORMATION: Description of Unknown Organism: This is a
      naturally occuring amino terminal peptide fragment
      derived from substance P.
<220> FEATURE:
<221> NAME/KEY: MOD_RES
<222> LOCATION: (1)..(4)
```

-continued

```
<223> OTHER INFORMATION: This sequence is made up by the first four
      amino acids of substance P.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<303> JOURNAL: Nature
<304> VOLUME: 262
<306> PAGES: 784-785
<307> DATE: 1986
<300> PUBLICATION INFORMATION:
<303> JOURNAL: J. Neurosci.
<304> VOLUME: 10
<306> PAGES: 1309-1318
<307> DATE: 1990

<400> SEQUENCE: 11

Arg Pro Lys Pro
 1

<210> SEQ ID NO 12
<211> LENGTH: 7
<212> TYPE: PRT
<213> ORGANISM: Unknown Organism
<220> FEATURE:
<223> OTHER INFORMATION: Description of Unknown Organism: This is a
      naturally occuring amino thermal peptide fragment
      derived from substance P.
<220> FEATURE:
<221> NAME/KEY: MOD_RES
<222> LOCATION: (1)..(7)
<223> OTHER INFORMATION: This fragment is made up of the first seven
      amino acids of substance P.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<303> JOURNAL: Nature
<304> VOLUME: 262
<306> PAGES: 784-785
<307> DATE: 1986
<300> PUBLICATION INFORMATION:
<303> JOURNAL: J. Neurosci.
<304> VOLUME: 10
<306> PAGES: 1309-1318
<307> DATE: 1990

<400> SEQUENCE: 12

Arg Pro Lys Pro Gln Gln Phe
 1               5

<210> SEQ ID NO 13
<211> LENGTH: 9
<212> TYPE: PRT
<213> ORGANISM: Unknown Organism
<220> FEATURE:
<223> OTHER INFORMATION: Description of Unknown Organism: This is a
      naturally occuring amino thermal peptide fragment
      derived from substance P.
<220> FEATURE:
<221> NAME/KEY: MOD_RES
<222> LOCATION: (1)..(9)
<223> OTHER INFORMATION: This fragment is made of the first nine amino
      acids of substance P.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<303> JOURNAL: Nature
<304> VOLUME: 262
<306> PAGES: 784-785
<307> DATE: 1986
```

```
<300> PUBLICATION INFORMATION:
<303> JOURNAL: J. Neurosci.
<304> VOLUME: 10
<306> PAGES: 1309-1318
<307> DATE: 1990

<400> SEQUENCE: 13

Arg Pro Lys Pro Gln Gln Phe Phe Gly
 1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: This is an
      analog of substance P
<220> FEATURE:
<221> NAME/KEY: MOD_RES
<222> LOCATION: (2)
<223> OTHER INFORMATION: Xaa at position 2 is D-form of Proline;
<220> FEATURE:
<221> NAME/KEY: MOD_RES
<222> LOCATION: (7)
<223> OTHER INFORMATION: Xaa in position 7 is D-form of Phenylalanine;
<220> FEATURE:
<221> NAME/KEY: MOD_RES
<222> LOCATION: (9)
<223> OTHER INFORMATION: Xaa in position 9 is D-form of Tryptophan;
<220> FEATURE:
<221> NAME/KEY: MOD_RES
<222> LOCATION: (11)
<223> OTHER INFORMATION: Xaa in position 11 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
      Dam, T.V.
<303> JOURNAL: Regulatory Peptides
<304> VOLUME: 22
<306> PAGES: 18-
<307> DATE: 1988

<400> SEQUENCE: 14

Arg Xaa Lys Pro Gln Gln Xaa Phe Xaa Leu Xaa
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: This is an
      analog of substance P
<220> FEATURE:
<221> NAME/KEY: MOD_RES
<222> LOCATION: (2)
<223> OTHER INFORMATION: Xaa in position 2 is D-form of Proline;
<220> FEATURE:
<221> NAME/KEY: MOD_RES
<222> LOCATION: (7)
<223> OTHER INFORMATION: Xaa in position 7 is D-form of Phenylalanine;
<220> FEATURE:
<221> NAME/KEY: MOD_RES
<222> LOCATION: (9)
<223> OTHER INFORMATION: Xaa in position 9 is D-form of Tryptophan;
<300> PUBLICATION INFORMATION:
```

```
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 15

Arg Xaa Lys Pro Gln Gln Xaa Phe Xaa Leu Met Gly
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: This is an
      analog of substance P
<220> FEATURE:
<221> NAME/KEY: MOD_RES
<222> LOCATION: (2)
<223> OTHER INFORMATION: Xaa in position 2 is D-form of Proline;
<220> FEATURE:
<221> NAME/KEY: MOD_RES
<222> LOCATION: (7)
<223> OTHER INFORMATION: Xaa in position 7 is D-form of Tryptophan;
<220> FEATURE:
<221> NAME/KEY: MOD_RES
<222> LOCATION: (9)
<223> OTHER INFORMATION: Xaa in position 9 is D-form of Tryptophan;
<220> FEATURE:
<221> NAME/KEY: MOD_RES
<222> LOCATION: (11)
<223> OTHER INFORMATION: Xaa in position 11 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 16

Arg Xaa Lys Pro Gln Gln Xaa Phe Xaa Leu Xaa
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: This is an
      analog of substance P
<220> FEATURE:
<221> NAME/KEY: MOD_RES
```

-continued

```
<222> LOCATION: (2)
<223> OTHER INFORMATION: Xaa in position 2 is D-form of Proline;
<220> FEATURE:
<221> NAME/KEY: MOD_RES
<222> LOCATION: (7)
<223> OTHER INFORMATION: Xaa in position 7 is D-form of Tryptophan;
<220> FEATURE:
<221> NAME/KEY: MOD_RES
<222> LOCATION: (9)
<223> OTHER INFORMATION: Xaa in position 9 is D-form of Tryptophan;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 17

Arg Xaa Lys Pro Gln Gln Xaa Phe Xaa Leu Met Gly
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: This is an
      analog of substance P.
<220> FEATURE:
<221> NAME/KEY: MOD_RES
<222> LOCATION: (11)
<223> OTHER INFORMATION: Xaa at position 11 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 18

Arg Pro Cys Pro Gln Cys Phe Tyr Gly Pro Xaa
 1               5                  10
```

I claim:

1. A method for treating bone tumor pain, the method comprising the step of administering to a subject a therapeutically effective amount of a botulinum toxin component, wherein the component comprises both a proteolytic domain and an H chain, but does not contain an $H_C$ with a presynaptic binding function, covalently coupled to substance P, thereby alleviating bone tumor pain.

2. The method of claim 1 wherein the botulinum toxin component is a botulinum toxin selected from the group consisting of serotype A, serotype B, serotype $C_1$, serptype D, serotype E, serotype F and serotype G, wherein the component does not contain an $H_C$ capable of presynaptic binding.

3. The method of claim 1 wherein the botulinum toxin component is botulinum toxin serotype A.

4. The method of claim 1 wherein the botulinum toxin component comprises an $LH_N$.

5. The method of claim 4 wherein the $H_N$ is obtained from a botulinum toxin selected from the group consisting of botulinum toxin serotype A, serotype B, serotype $C_1$, serotype D, serotype E, serotype F and serotype G.

6. The method of claim 4 wherein the L is obtained from a botulinum toxin selected from the group consisting of botulinum toxin serotype A, serotype B, serotype $C_1$, serotype D, serotype E, serotype F and serotype G.

7. A method for treating bone tumor pain, the method comprising the step of administering to a subject a therapeutically effective amount of a botulinum toxin type A proteolytic domain covalently attached to a botulinum toxin type A translocational domain that is covalently attached to substance P, thereby alleviating bone tumor pain.

8. A method for treating pain in a subject with Osteoid Osteoma or Osteoblastoma, the method comprising the step of administering to a subject a therapeutically effective amount of $LH_N$ covalently coupled to substance P wherein $LH_N$ is obtained from botulinum toxin serotype A, B, $C_1$, D, E, F or G, thereby alleviating pain due to Osteoid Osteoma or Osteoblastoma.

* * * * *